United States Patent [19]

Delaunois et al.

[11] 4,125,560

[45] Nov. 14, 1978

[54] AROMATIC AMINES SYNTHESIS PROCESS AND PRODUCTS RESULTING FROM APPLICATION OF THIS PROCESS

[75] Inventors: Claude L. Delaunois, Brussels; Willy O. De Graeve, Waterloo, both of Belgium

[73] Assignee: Universite Libre de Bruxelles Faculte des Sciences Appliquees, Brussels, Belgium

[21] Appl. No.: 705,577

[22] Filed: Jul. 15, 1976

[30] Foreign Application Priority Data

Aug. 20, 1973 [BE] Belgium .................................. 803763

[51] Int. Cl.² ............................................. C07C 85/06
[52] U.S. Cl. ..................................... 260/581; 568/805; 568/716
[58] Field of Search ................. 260/581, 621 D, 621 E

[56] References Cited

U.S. PATENT DOCUMENTS

| | | | |
|---|---|---|---|
| 1,820,908 | 9/1931 | Cross | 260/621 D |
| 2,000,410 | 5/1935 | Morrell et al. | 260/581 X |
| 2,128,700 | 8/1938 | Frye | 260/581 |
| 2,894,988 | 7/1959 | Cryer | 260/581 |
| 3,931,298 | 1/1976 | Wollensak | 260/581 |
| 3,960,962 | 6/1976 | Shubkin | 260/581 |

FOREIGN PATENT DOCUMENTS 619,877 3/1949 United Kingdom ..................... 260/581

OTHER PUBLICATIONS

Shreve, "Chemical Process Industries", 3rd Ed., (1965).

*Primary Examiner*—Winston A. Douglas
*Assistant Examiner*—John J. Doll
*Attorney, Agent, or Firm*—Bacon & Thomas

[57] ABSTRACT

The invention pertains to an aromatic amines synthesis process, fundamentally characterized by the fact that it consists of carrying out the ammonolysis of phenols under pressure in liquid phase by ammonia in aqueous solution.

12 Claims, No Drawings

AROMATIC AMINES SYNTHESIS PROCESS AND PRODUCTS RESULTING FROM APPLICATION OF THIS PROCESS

This is a continuation of application Ser. No. 488,901, filed July 16, 1974, now abandoned.

This invention refers to the ammonolysis of phenols with a view to the extraction of products which are of industrial and commercial interest. Its object is a process for the direct amination of phenols with amines, whereas the more usual processes require the prior transformation of aromatic hydrocarbons, benzene for instance, into intermediate compounds, nitro (nitrobenzene) or chloro (chlorobenzene) derivatives.

It is known, for example, that the hydrogenation of nitro derivatives gives the corresponding amines. Chloro-derivatives can be subjected to reaction with ammonia to give amines.

It is also known that it is possible to obtain amines by reaction between ammonia and alcohols and that the reaction between aromatic alcohols called phenols is generally affected either in a gaseous phase in the presence of catalysts and anhydrous ammonia or in the liquid phase in the presence of liquefied anhydrous ammonia. Industrially speaking, these processes have various drawbacks arising primarily out of deterioration of the catalysts, which necessitates the frequent regeneration thereof.

The fabrication of meta-aminophenols from resorcin is also known. This is a diphenol and it is well known that its reactivity is greater than that of monophenols.

As a result of the amination, mixed aminophenol compounds are obtained — not a simple amine.

Finally, it will be observed that a further advantage of the process according to the invention is that isomerization, degradation of heavy phenols (alkylated phenols) into lighter phenols and their amination can be effected simultaneously.

Consequently, the aromatic amines synthesis process which is the subject of this invention is fundamentally characterized by the fact that it consists of effecting the phenol ammonolysis under pressure in liquid phase by ammonia in aqueous solution. This ammonolysis is catalyzed by the presence of soluble, adequate ammonium salts in the aqueous solution. Thus there is simultaneously amination, degradation and isomerization of heavy phenols into light phenols.

In a range of applications, the pressure can be between 50 and 2000 kg/cm2, the temperature can be between 400° and 550° C and the contact time can vary from a few minutes to 8 hours. These quantitative data form parameters which the operator can easily determine prorata to the applications of the process.

The advantages resulting from application of this process are numerous and substantial. The reaction can give yields of around 50% of amines without catalyst. This yield is expressed as a percentage in weight of the phenols treated.

The economic interest of the process is better shown if the yield of amines obtained is expressed in percentage in relation to the phenol which has reacted and which is therefore converted into other compounds.

The phenol which has not reacted is simply recycled in the process, as is the current industrial practice.

In the case of the phenol ($C_6H_5OH$) mentioned here as an example, treatment of a 25% ammonia aqueous solution, containing 31% phenol, at 440° C and 1000 kg/cm2 pressure, enables the obtention of 32% aniline for 43% phenol consumed. The yield in relation to the phenol consumed is therefore 74.4%.

The influence of the pressure has been demonstrated. Under the same conditions of temperature and concentrations of the phenol ammonia aqueous solution, only 4% aniline is obtained at 400 kg/cm2, 14% at 600 kg/cm2, 24% at 800 kg/cm2 and, as stated above, 32% at 1000 kg/cm2. Nevertheless, the possibility of working with an aqueous solution makes it possible to employ a very wide range of catalysts and to utilize them in solution in the form of salts soluble in water. This eliminates the necessity for regenerating the solid catalyst as in the case in gaseous phase.

In the process using anhydrous ammonia, the catalysts are only slightly soluble or are insoluble. On the contrary, in the process according to the invention, the ammonia aqueous solution readily dissolves a large number of mineral salts capable of being used as catalysts. The unreacted aqueous solution of ammonia and catalyst not having reacted, can subsequently be recycled.

The influence of an adequate mineral catalyst, soluble in the aqueous ammonia solution of phenol, on the reaction rate, is shown by the following example.

Ammonium chloride ($NH_4Cl$) was used as a catalysts in different concentrations in weight in relation to the phenol.

In the chosen example, a 5% ammonium chloride concentration was used. At 440° C and 1000 kg/cm2, for the same concentrations of phenol in ammonia aqueous solution as those mentioned in the preceding example, 66.4% aniline was obtained after an hours contact for 71.8% phenol disappeared. In this case, the amination yield in relation to the phenol disappeared is 92.75%.

The reaction temperature influences amine formation.

In the experimental conditions mentioned above, only 27.8% aniline is obtained at 380°, 43.3% at 400°, 57% at 420° C and, as indicated, 66.4% at 440° C.

The advantages of industrial application of the process according to the invention appear even better if certain specific cases are considered, for example in the treatment of heavy phenols, even more particularly, for instance, from the angle of the valorization of the phenolic fraction of coking tars at low temperatue. In effect, knowledge of the different aspects of ammonolysis makes it possible to determine to what extent and under what conditions it is possible to achieve the thermal degradation of heavy phenols into light phenols and their simultaneous amination in aqueous phase, under pressure.

Generally speaking, in applying the process according to the invention, at the same time as the amination reaction takes place, heavy phenols such as alkyls, and polyalkyl phenols and polyphenols, undergo degradation into lighter phenols and isomerization. These reactions are of great interest in view of the fact that light phenols, phenic acid and cresols are particularly sought after for the production of a whole range of industrial products, in particular formo-phenolic resins, certain isomers, cresols and xylenols.

The result is that, by isomerization, the lesser used phenols are brought to a form that is more in demand and is of great economic interest.

In the case of para-cresol, mentioned here as an example of treatment of a monoalkylated phenol, for 33.7% of para-cresol in a 25% ammonia aqueous solution, we get, in the presence of 2.4% of NH₄Cl at 440° C and 1000 kg/cm2, 9% isomerization of the para-cresol in ortho and meta-cresol, 8.6% phenol and 11.6% xylenol isomers, 12% toluidines, 5% aniline and 3.5% xylidines.

27% para-cresol is not transformed and can be recycled.

Treatment, under experimental conditions, of identical concentrations of 2,4 xylenol, mentioned as an example of polyalkyl phenols, gives, for a 31.8 residual percentage of non-transformed 2,4 xylenol, an isomerization of 19.2% in 2,6 and 3,4 xylenols principally, 10.7% cresols, 1.8% phenol. 3% trimethyl phenols and 11.9% amines, of which 6.15% of 2,4 xylidine and 2.43% of other xylidine isomers.

Systematically, therefore, application of the process according to the invention to the treatment of heavy phenols gives lighter phenol amines, more advantageous phenol isomers and lighter phenols. Working in an ammonia aqueous medium considerably retrogrades reactions by dehydroxylation of phenols in aromatic hydrocarbons. One particularly interesting case is the application of the process according to the invention to the phenolic fraction of tars obtained by coking coal, lignites or peat at low temperatures. In the case of coal, tars that are rich in heavy phenols are obtained under these conditions. These are perhaps of less industrial value but they can be transformed into amines or light phenols. The polyphenols present in particular in lignite tar give lighter phenols and polyamines.

It goes without saying, of course, that by adjusting the ammonolysis temperature, the pressure and reaction time, the proportion of amines and phenols it is desired to obtain can be varied.

The invention concerns both the synthesis process revealed herein and any applications of this process, as well as any products obtained by employing the said process in the said applications.

What we claim is:

1. An aromatic amines synthesis process which comprises the ammonolysis of alkyl or polyalkyl phenols in a liquid phase by an aqueous ammonia solution containing dissolved therein a catalytic amount of an ammonium salt, said ammonolysis being effected at a temperature of from 400°–550° C and under a pressure of from 800–2,000kg/cm² to simultaneously degrade, isomerize and aminate said phenols.

2. The process of claim 1 wherein the aqueous ammonium solution is a 25% aqueous ammonium solution.

3. The process of claim 1 wherein the ammonium salt is ammonium chloride.

4. The process of claim 1, wherein the pressure is between 1000 and 2000 kg/cm², and said catalyst is ammonium chloride.

5. The process of claim 4, wherein said phenols are degraded and isomerized into lighter phenols.

6. The process of claim 5, wherein the phenols are obtained from the phenolic fraction of tars obtained from coking coal, lignites or peat at low temperatures.

7. The process of claim 4 wherein the phenol is para-cresol.

8. The process of claim 5 wherein the phenol is 2,4 xylenol.

9. The process of claim 7, wherein ortho cresol, meta cresol, phenol, xylenols, toluidines, aniline and xylidines are produced.

10. The process of claim 8, wherein 2, 6 and 3, 4 xylenols; cresols; phenol; trimethyl phenols, and xylidines are produced.

11. An aromatic amines synthesis process which consists essentially of the ammonolysis of alkyl or polyalkyl phenols in a liquid phase by an aqueous ammonium solution containing dissolved therein a catalytic amount of an ammonium salt, said ammonolysis being effected at a temperature of from 400°–550° C and under a pressure of from 800–2,000kg/cm² to simultaneously degrade, isomerize and aminate said phenols.

12. The process of claim 11, wherein the pressure is from 1000–2000 kg/cm² and the ammonium salt is ammonium chloride at a concentration of 5%.

* * * * *